US010748657B2

(12) United States Patent
Eggebraaten et al.

(10) Patent No.: US 10,748,657 B2
(45) Date of Patent: Aug. 18, 2020

(54) RATIONALE GENERATION MANAGEMENT

(71) Applicant: INTERNATIONAL BUSINESS MACHINES CORPORATION, Armonk, NY (US)

(72) Inventors: Thomas J. Eggebraaten, Rochester, MN (US); Marie L. Setnes, Bloomington, MN (US)

(73) Assignee: International Business Machines Corporation, Armonk, NY (US)

( * ) Notice: Subject to any disclaimer, the term of this patent is extended or adjusted under 35 U.S.C. 154(b) by 555 days.

(21) Appl. No.: 15/588,732

(22) Filed: May 8, 2017

(65) Prior Publication Data
US 2018/0322252 A1 Nov. 8, 2018

(51) Int. Cl.
*G16H 50/20* (2018.01)
*G16H 20/00* (2018.01)
*G16H 10/20* (2018.01)
*G16H 50/70* (2018.01)
*G06F 19/00* (2018.01)

(52) U.S. Cl.
CPC .......... *G16H 50/20* (2018.01); *G06F 19/3481* (2013.01); *G16H 10/20* (2018.01); *G16H 20/00* (2018.01); *G16H 50/70* (2018.01)

(58) Field of Classification Search
CPC ........ G16H 50/20; G16H 50/70; G16H 20/00; G16H 10/20; G06F 19/3481
See application file for complete search history.

(56) References Cited

U.S. PATENT DOCUMENTS

| 8,762,177 | B2 | 6/2014 | Dahan |
| 9,563,745 | B2 * | 2/2017 | Saigal .................... G06N 5/048 |
| 2003/0163353 | A1 * | 8/2003 | Luce .................. G06F 19/3418 |
| | | | 705/2 |
| 2008/0082410 | A1 | 4/2008 | Zhou et al. |

(Continued)

FOREIGN PATENT DOCUMENTS

| CN | 102609405 A | 7/2012 |
| WO | 9926172 A1 | 5/1999 |
| WO | 2016103036 A1 | 6/2016 |

OTHER PUBLICATIONS

IBM: List of IBM Patents or Patent Applications Treated As Related (Appendix P), Sep. 15, 2017, pp. 1-2.

(Continued)

*Primary Examiner* — Eliza A Lam
(74) *Attorney, Agent, or Firm* — Jordan T. Schiller

(57) ABSTRACT

Disclosed aspects relate to generating rationales for treatment options. A set of preference scores that indicates a first preference score for a first treatment option of a set of treatment options may be received. A rank-order that indicates a first ranking for the first treatment option may be received. The set of preference scores may be analyzed with respect to the rank-order to determine a relationship between the first preference score and the first ranking for the first treatment option. Based on the relationship between the first preference score and the first ranking, a set of rationale data for the first treatment option may be generated with respect to the first rank. Based on a user profile for a user, the set of rationale data may be configured for the user. The set of rationale data which is configured for the user may be provided.

20 Claims, 8 Drawing Sheets

(56) References Cited

U.S. PATENT DOCUMENTS

| | | | |
|---|---|---|---|
| 2010/0191100 A1* | 7/2010 | Anderson | A61B 5/055 600/424 |
| 2012/0016206 A1* | 1/2012 | Ramarajan | G06Q 50/22 600/300 |
| 2012/0016690 A1 | 1/2012 | Ramarajan et al. | |
| 2012/0301864 A1 | 11/2012 | Bagchi et al. | |
| 2013/0325502 A1 | 12/2013 | Robicsek et al. | |
| 2014/0316813 A1 | 10/2014 | Bauer | |
| 2016/0015995 A1 | 1/2016 | Leung et al. | |
| 2016/0078182 A1 | 3/2016 | Allen et al. | |
| 2016/0188813 A1 | 6/2016 | Hennenfent | |

OTHER PUBLICATIONS

Eggebraaten et al., U.S. Appl. No. 15/704,587, filed Sep. 14, 2017, titled "Rationale Generation Management," pp. 1-55.

* cited by examiner

700

| Preference Score | Treatment Rank |
|---|---|
| 7-10 (High) | Recommended (Green) |
| 4-6 (Medium) | For consideration (Yellow) |
| 1-3 (Low) | Not recommended (Red) |

| Preference Score | Treatments Scored Green | Treatments Scored Yellow | Treatments Scored Red |
|---|---|---|---|
| High | Summarize Attributes | Summarize Attributes + Exclusion Factors | Summarize Attributes + Exclusion Factors |
| Medium | Summarize Attributes + Rationale for preferred treatment exclusions | Summarize Attributes | Summarize Attributes + Exclusion Factors |
| Low | Summarize Attributes + Rationale for preferred treatment exclusions | Summarize Attributes + Rationale for preferred treatment exclusions | Summarize Attributes |

FIG. 8

RATIONALE GENERATION MANAGEMENT

BACKGROUND

This disclosure relates generally to computer systems and, more particularly, relates to rationale generation management. The amount of data that needs to be managed is increasing. Management of data may be desired to be performed as efficiently as possible. As data needing to be managed increases, the need for rationale generation management may also increase.

SUMMARY

Aspects of the disclosure relate to generating rationale data for a set of treatment options. Treatment options for a user may be ranked based on a set of attributes, and a set of rationale data may be dynamically provided for each treatment option of the set of treatment options. The set of rationale data may be configured for a user based on a user profile. The set of rationale data may include an indication of why a treatment option was ranked where it was, as well as a candidate rank that indicates where the treatment option would be ranked absent one or more exclusion factors. The set of rationale data may take into account the factors used to determine the rank for a treatment option as well as the factors used to determine the rank for other treatment options of the set of treatment options. For instance, if a particular treatment option is scored as the top-ranked answer of the set of treatment options, the set of rationale data may indicate the reasons why it is preferred over other treatment options. In embodiments, generating the set of rationale data may include summarizing the attributes that lead to a particular ranking for a treatment option, summarizing the attributes as well as exclusion factors that lowered the ranking of a treatment option, or summarizing the attributes and rationale for preferred treatment exclusions.

Disclosed aspects relate to generating rationales for treatment options. A set of preference scores that indicates a first preference score for a first treatment option of a set of treatment options may be received. A rank-order that indicates a first ranking for the first treatment option may be received. The set of preference scores may be analyzed with respect to the rank-order to determine a relationship between the first preference score and the first ranking for the first treatment option. Based on the relationship between the first preference score and the first ranking, a set of rationale data for the first treatment option may be generated with respect to the first rank. Based on a user profile for a user, the set of rationale data may be configured for the user. The set of rationale data which is configured for the user may be provided.

The above summary is not intended to describe each illustrated embodiment or every implementation of the present disclosure.

BRIEF DESCRIPTION OF THE SEVERAL VIEWS OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure.

FIG. 7 depicts an example of generating rationales for a set of treatment options, according to embodiments.

FIG. 8 depicts an example of generating rationales for a set of treatment options, according to embodiments.

Figure 1:
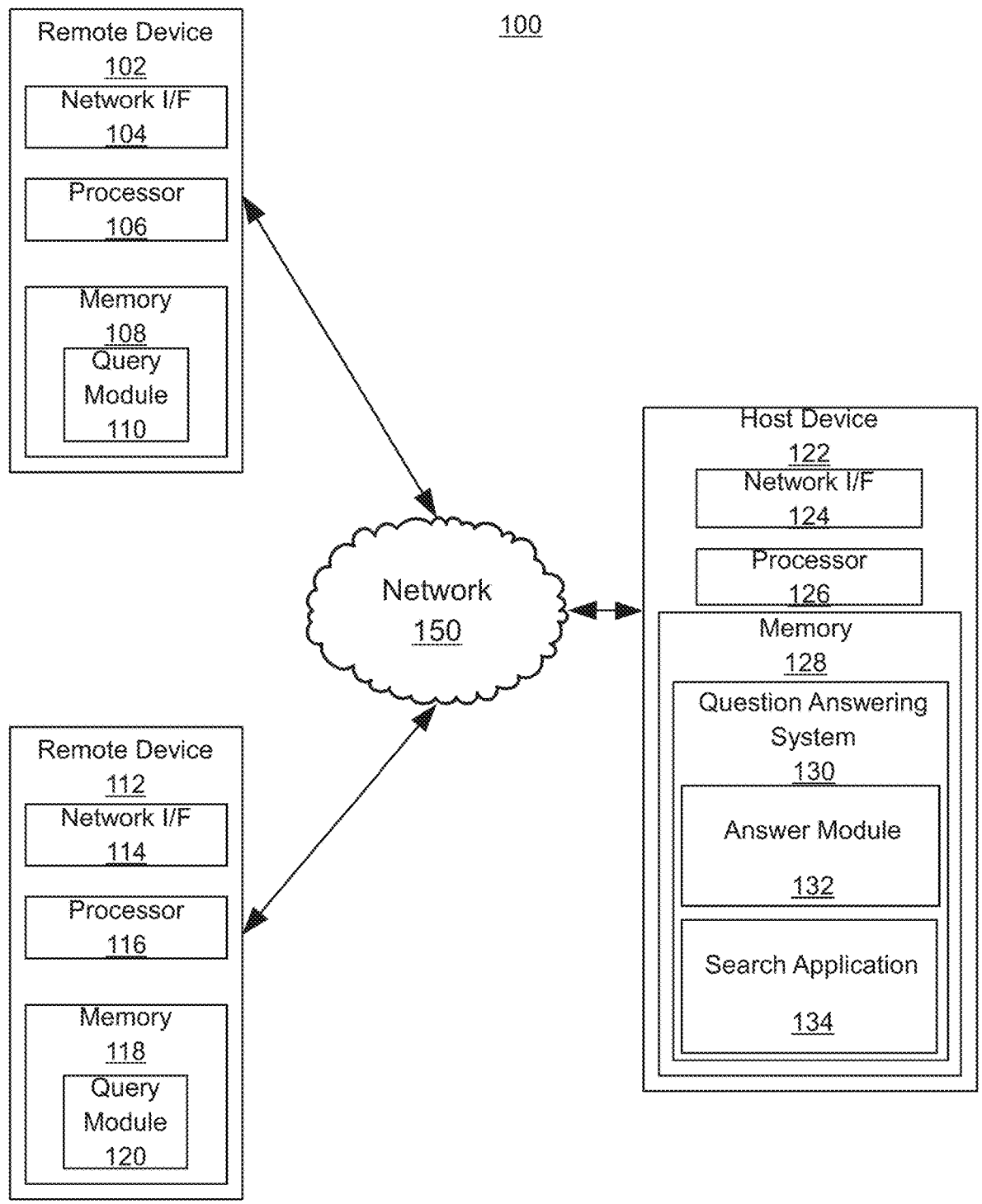
FIG. 1 is a diagrammatic illustration of an example computing environment, according to embodiments.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

Aspects of the disclosure relate to generating rationale data for a set of treatment options. Treatment options for a user (e.g., patient) may be ranked based on a set of attributes, and a set of rationale data may be dynamically provided for each treatment option of the set of treatment options. The set of rationale data may be configured (e.g., customized) for a user based on a user profile. The set of rationale data may include an indication of why a treatment option was ranked where it was, as well as a candidate rank that indicates where the treatment option would be ranked absent one or more exclusion factors. The set of rationale data may take into account the factors used to determine the rank for a treatment option as well as the factors used to determine the rank for other treatment options of the set of treatment options. For instance, if a particular treatment options is scored as the top-ranked answer of the set of treatment options, the set of rationale data may indicate the reasons why it is preferred over other treatment options. In embodiments, generating the set of rationale data may include summarizing the attributes that lead to a particular ranking for a treatment option, summarizing the attributes as well as exclusion factors that lowered the ranking of a treatment option, or summarizing the attributes and rationale for preferred treatment exclusions (e.g., why other treatment operations were preferred with respect to a particular treatment option). Leveraging rationale data with respect to a set of treatment options may be associated with benefits such as treatment option ranking validity, accuracy, and rationale generation efficiency.

Question answering systems are one tool that may be used to provide and rank treatment options for patients. Aspects of the disclosure relate to the recognition that, in some situations, question answering systems may be lacking with respect to provision of evidence-based rationales explaining how and why certain treatment options are ranked as they are. Accordingly, aspects of the disclosure relate to automatic generation of rationale data for a set of treatment options. A rank-order assigned to a set of treatment options may be evaluated with respect to a set of preference scores for the set of treatment options to indicate the degree to which the set of preference scores match the rank-order. Based on a relationship between the set of preference scores and the rank-order, a set of rationale data that indicates the attributes and factors that led to the ranking of a particular treatment option may be dynamically generated. As such, dynamic rationale generation may promote automated treatment option reliability and facilitate treatment option selection.

Aspects of the disclosure relate to a system, method, and computer program product for generating rationales for treatment options. A set of preference scores that indicates a first preference score for a first treatment option of a set of treatment options may be received. A rank-order that indicates a first ranking for the first treatment option may be received. The set of preference scores may be analyzed with respect to the rank-order to determine a relationship between the first preference score and the first ranking for the first treatment option. Based on the relationship between the first preference score and the first ranking, a set of rationale data for the first treatment option may be generated with respect to the first rank. Based on a user profile for a user, the set of rationale data may be configured for the user. The set of rationale data which is configured for the user may be provided.

In embodiments a set of attributes that characterize a merit feature of the set of treatment options may be detected to determine the relationship between the first preference score and the first ranking for the first treatment option. In embodiments a set of exclusion factors that characterize a demerit feature of the set of treatment options may be detected to determine the relationship between the first preference score and the first ranking for the first treatment option. In embodiments, it may be determined that the first preference scores achieves a match with respect to the first ranking based on the relationship between the first preference score and the first ranking, and a first subset of attributes of the set of attributes that corresponds to the first treatment option of the set of treatment options may be compiled to generate the set of rationale data in an automated fashion. In embodiments, it may be determined that the first preference score fails to achieve a match with respect to the first ranking based on the relationship between the first preference score and the first ranking, and both a first subset of attributes of the set of attributes that corresponds to the first treatment option of the set of treatment options and a first subset of exclusion factors of the set of exclusions factors that corresponds to the first treatment option of the set of treatment options may be compiled to generate the set of rationale data in an automated fashion. In embodiments, it may be determined that the first preference score achieves a discrepancy threshold with respect to the first ranking based on the relationship between the first preference score and the first ranking, and both a second subset of attributes of the set of attributes that corresponds to a second treatment option of the set of treatment options and a second subset of exclusion factors of the set of exclusion factors that corresponds to the second treatment option of the set of treatment options may be compiled to generate the set of rationale data in an automated fashion. In embodiments, the set of attributes may be filtered in an automated fashion based on a set of attribute priority criteria to remove a second subset of attributes from the set of attributes. Altogether, performance or efficiency benefits with respect to rationale generation management may occur. Aspects may save resources such as bandwidth, processing, or memory.

Turning now to the figures, FIG. 1 is a diagrammatic illustration of an exemplary computing environment, consistent with embodiments of the present disclosure. In certain embodiments, the environment 100 can include one or more remote devices 102, 112 and one or more host devices 122. Remote devices 102, 112 and host device 122 may be distant from each other and communicate over a network 150 in which the host device 122 comprises a central hub from which remote devices 102, 112 can establish a communication connection. Alternatively, the host device and remote devices may be configured in any other suitable relationship (e.g., in a peer-to-peer or other relationship).

In certain embodiments the network 100 can be implemented by any number of any suitable communications media (e.g., wide area network (WAN), local area network (LAN), Internet, Intranet, etc.). Alternatively, remote devices 102, 112 and host devices 122 may be local to each other, and communicate via any appropriate local communication medium (e.g., local area network (LAN), hardwire, wireless link, Intranet, etc.). In certain embodiments, the network 100 can be implemented within a cloud computing environment, or using one or more cloud computing services. Consistent with various embodiments, a cloud computing environment can include a network-based, distributed data processing system that provides one or more cloud computing services. In certain embodiments, a cloud computing environment can include many computers, hundreds or thousands of them, disposed within one or more data centers and configured to share resources over the network.

In certain embodiments, host device 122 can include a question answering system 130 (also referred to herein as a QA system) having a search application 134 and an answer module 132. In certain embodiments, the search application may be implemented by a conventional or other search engine, and may be distributed across multiple computer systems. The search application 134 can be configured to search one or more databases or other computer systems for content that is related to a question input by a user at a remote device 102, 112.

In certain embodiments, remote devices 102, 112 enable users to submit questions (e.g., search requests or other queries) to host devices 122 to retrieve search results. For example, the remote devices 102, 112 may include a query module 120 (e.g., in the form of a web browser or any other suitable software module) and present a graphical user (e.g., GUI, etc.) or other interface (e.g., command line prompts, menu screens, etc.) to solicit queries from users for submission to one or more host devices 122 and further to display answers/results obtained from the host devices 122 in relation to such queries.

Consistent with various embodiments, host device 122 and remote devices 102, 112 may be computer systems preferably equipped with a display or monitor. In certain embodiments, the computer systems may include at least one processor 106, 116, 126 memories 108, 118, 128 and/or internal or external network interface or communications devices 104, 114, 124 (e.g., modem, network cards, etc.), optional input devices (e.g., a keyboard, mouse, or other input device), and any commercially available and custom software (e.g., browser software, communications software, server software, natural language processing software, search engine and/or web crawling software, filter modules for filtering content based upon predefined criteria, etc.). In certain embodiments, the computer systems may include server, desktop, laptop, and hand-held devices. In addition, the answer module 132 may include one or more modules or units to perform the various functions of present disclosure embodiments described below (e.g., receiving an input question, evaluating the quality of the input question, assigning a set of quality values, and generating an icon), and may be implemented by any combination of any quantity of software and/or hardware modules or units.

Figure 2:
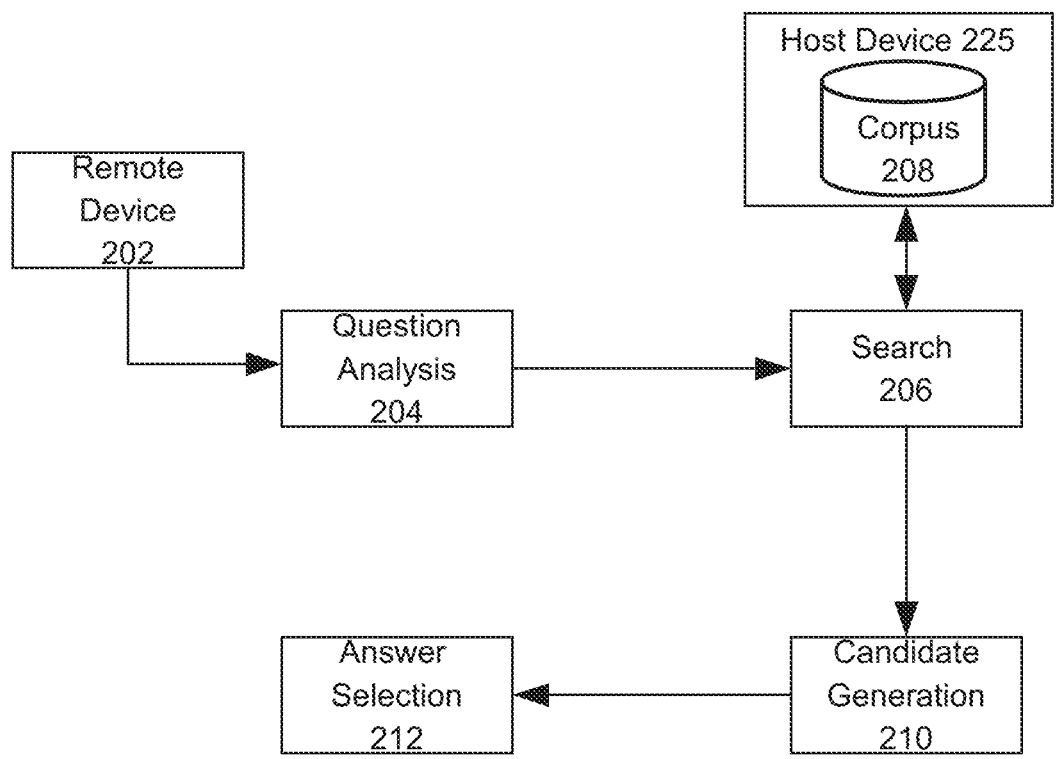
FIG. 2 is a system diagram depicting a high level logical architecture for a question answering system, according to embodiments.

FIG. 2 is a system diagram depicting a high-level logical architecture 200 for a question answering system (also referred to herein as a QA system), consistent with embodiments of the present disclosure. Aspects of FIG. 2 are directed toward components for use with a QA system. In certain embodiments, the question analysis component 204 can receive a natural language question from a remote device 202, and can analyze the question to produce, minimally, the semantic type of the expected answer. The search component 206 can formulate queries from the output of the question analysis component 204 and may consult various resources such as the internet or one or more knowledge resources, e.g., databases, corpora 208, to retrieve documents, passages, web-pages, database tuples, etc., that are relevant to answering the question. For example, as shown in FIG. 2, in certain embodiments, the search component 206 can consult a corpus of information 208 on a host device 225. The candidate answer generation component 210 can then extract from the search results potential (candidate) answers to the question, which can then be scored and ranked by the answer selection component 212 which may produce a final ranked list of answers with associated confidence measure values.

The various components of the exemplary high level logical architecture for a QA system described above may be used to implement various aspects of the present disclosure. For example, the question analysis component 204 could, in certain embodiments, be used to process a natural language question for which relevant images can be provided. Further, the search component 206 can, in certain embodiments, be used to perform a search of a corpus of information 208 for a set of images that are related to an answer to an input question to the QA system. The candidate generation component 210 can be used to identify a set of candidate images based on the results of the search component 206. Further, the answer selection component 212 can, in certain embodiments, be used to determine and select a subset of the set of candidate images to provide in a display area. In certain embodiments, the determination of the subset of the candidate images can be based on a confidence value of the set of images and a designated display specification.

Figure 3:
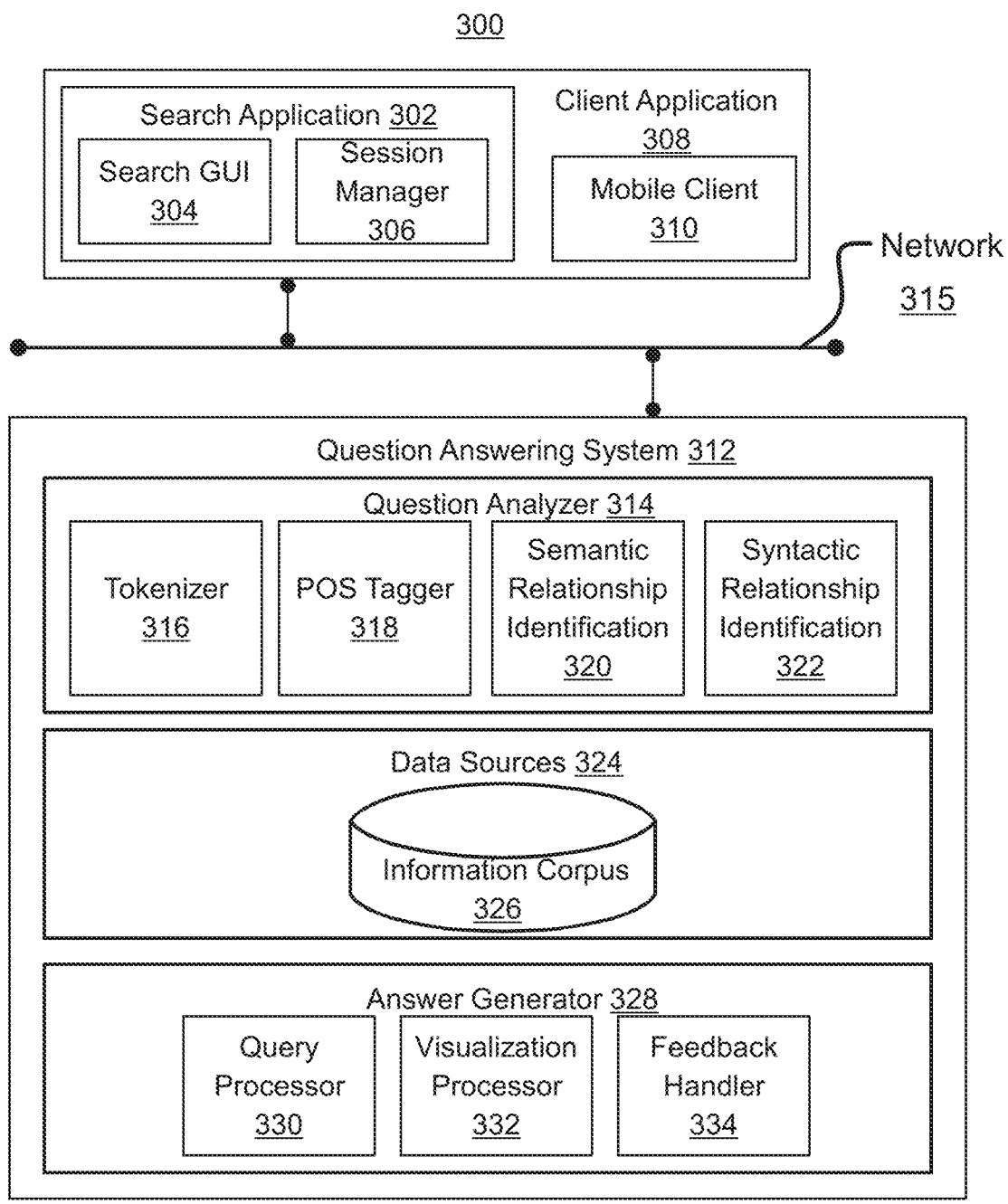
FIG. 3 is a block diagram illustrating a question answering system to generate answers to one or more input questions, according to embodiments.

FIG. 3 is a block diagram illustrating a question answering system (also referred to herein as a QA system) to generate answers to one or more input questions, consistent with various embodiments of the present disclosure. Aspects of FIG. 3 are directed toward an exemplary system architecture 300 of a question answering system 312 to generate answers to queries (e.g., input questions). In certain embodiments, one or more users may send requests for information to QA system 312 using a remote device (such as remote devices 102, 112 of FIG. 1). QA system 312 can perform methods and techniques for responding to the requests sent by one or more client applications 308. Client applications 308 may involve one or more entities operable to generate events dispatched to QA system 312 via network 315. In certain embodiments, the events received at QA system 312 may correspond to input questions received from users, where the input questions may be expressed in a free form and in natural language.

A question (similarly referred to herein as a query) may be one or more words that form a search term or request for data, information or knowledge. A question may be expressed in the form of one or more keywords. Questions may include various selection criteria and search terms. A question may be composed of complex linguistic features, not only keywords. However, keyword-based search for answer is also possible. In certain embodiments, using unrestricted syntax for questions posed by users is enabled. The use of restricted syntax results in a variety of alternative expressions for users to better state their needs.

Consistent with various embodiments, client applications 308 can include one or more components such as a search application 302 and a mobile client 310. Client applications 308 can operate on a variety of devices. Such devices include, but are not limited to, mobile and handheld devices, such as laptops, mobile phones, personal or enterprise digital assistants, and the like; personal computers, servers, or other computer systems that access the services and functionality provided by QA system 312. For example, mobile client 310 may be an application installed on a mobile or other hand-held device. In certain embodiments, mobile client 310 may dispatch query requests to QA system 312.

Consistent with various embodiments, search application 302 can dispatch requests for information to QA system 312. In certain embodiments, search application 302 can be a client application to QA system 312. In certain embodiments, search application 302 can send requests for answers to QA system 312. Search application 302 may be installed on a personal computer, a server or other computer system. In certain embodiments, search application 302 can include a search graphical user interface (GUI) 304 and session manager 306. Users may enter questions in search GUI 304. In certain embodiments, search GUI 304 may be a search box or other GUI component, the content of which represents a question to be submitted to QA system 312. Users may authenticate to QA system 312 via session manager 306. In certain embodiments, session manager 306 keeps track of user activity across sessions of interaction with the QA system 312. Session manager 306 may keep track of what questions are submitted within the lifecycle of a session of a user. For example, session manager 306 may retain a succession of questions posed by a user during a session. In certain embodiments, answers produced by QA system 312 in response to questions posed throughout the course of a user session may also be retained. Information for sessions managed by session manager 306 may be shared between computer systems and devices.

In certain embodiments, client applications 308 and QA system 312 can be communicatively coupled through network 315, e.g. the Internet, intranet, or other public or private computer network. In certain embodiments, QA system 312 and client applications 308 may communicate by using Hypertext Transfer Protocol (HTTP) or Representational State Transfer (REST) calls. In certain embodiments, QA system 312 may reside on a server node. Client applications 308 may establish server-client communication with QA system 312 or vice versa. In certain embodiments, the network 315 can be implemented within a cloud computing environment, or using one or more cloud computing services. Consistent with various embodiments, a cloud computing environment can include a network-based, distributed data processing system that provides one or more cloud computing services.

Consistent with various embodiments, QA system 312 may respond to the requests for information sent by client applications 308, e.g., posed questions by users. QA system 312 can generate answers to the received questions. In certain embodiments, QA system 312 may include a question analyzer 314, data sources 324, and answer generator 328. Question analyzer 314 can be a computer module that analyzes the received questions. In certain embodiments, question analyzer 314 can perform various methods and techniques for analyzing the questions syntactically and semantically. In certain embodiments, question analyzer 314 can parse received questions. Question analyzer 314 may include various modules to perform analyses of received questions. For example, computer modules that question analyzer 314 may include, but are not limited to a tokenizer 316, part-of-speech (POS) tagger 318, semantic relationship identification 320, and syntactic relationship identification 322.

Consistent with various embodiments, tokenizer 316 may be a computer module that performs lexical analysis. Tokenizer 316 can convert a sequence of characters into a sequence of tokens. Tokens may be string of characters typed by a user and categorized as a meaningful symbol. Further, in certain embodiments, tokenizer 316 can identify word boundaries in an input question and break the question or any text into its component parts such as words, multi-word tokens, numbers, and punctuation marks. In certain embodiments, tokenizer 316 can receive a string of characters, identify the lexemes in the string, and categorize them into tokens.

Consistent with various embodiments, POS (part of speech) tagger 318 can be a computer module that marks up a word in a text to correspond to a particular part of speech. POS tagger 318 can read a question or other text in natural language and assign a part of speech to each word or other token. POS tagger 318 can determine the part of speech to which a word corresponds based on the definition of the word and the context of the word. The context of a word may be based on its relationship with adjacent and related words in a phrase, sentence, question, or paragraph. In certain embodiments, context of a word may be dependent on one or more previously posed questions. Examples of parts of speech that may be assigned to words include, but are not limited to, nouns, verbs, adjectives, adverbs, and the like. Examples of other part of speech categories that POS tagger 318 may assign include, but are not limited to, comparative or superlative adverbs, wh-adverbs, conjunctions, determiners, negative particles, possessive markers, prepositions, wh-pronouns, and the like. In certain embodiments, POS tagger 316 can tag or otherwise annotates tokens of a question with part of speech categories. In certain embodiments, POS tagger 316 can tag tokens or words of a question to be parsed by QA system 312.

Consistent with various embodiments, semantic relationship identification 320 may be a computer module that can identify semantic relationships of recognized entities in questions posed by users. In certain embodiments, semantic relationship identification 320 may determine functional dependencies between entities, the dimension associated to a member, and other semantic relationships.

Consistent with various embodiments, syntactic relationship identification 322 may be a computer module that can identify syntactic relationships in a question composed of tokens posed by users to QA system 312. Syntactic relationship identification 322 can determine the grammatical structure of sentences, for example, which groups of words are associated as "phrases" and which word is the subject or object of a verb. In certain embodiments, syntactic relationship identification 322 can conform to a formal grammar.

In certain embodiments, question analyzer 314 may be a computer module that can parse a received query and generate a corresponding data structure of the query. For example, in response to receiving a question at QA system 312, question analyzer 314 can output the parsed question as a data structure. In certain embodiments, the parsed question may be represented in the form of a parse tree or other graph structure. To generate the parsed question, question analyzer 130 may trigger computer modules 132-144. Question analyzer 130 can use functionality provided by computer modules 316-322 individually or in combination. Additionally, in certain embodiments, question analyzer 130 may use external computer systems for dedicated tasks that are part of the question parsing process.

Consistent with various embodiments, the output of question analyzer 314 can be used by QA system 312 to perform a search of one or more data sources 324 to retrieve information to answer a question posed by a user. In certain embodiments, data sources 324 may include data warehouses, information corpora, data models, and document repositories. In certain embodiments, the data source 324 can be an information corpus 326. The information corpus 326 can enable data storage and retrieval. In certain embodiments, the information corpus 326 may be a storage mechanism that houses a standardized, consistent, clean and integrated form of data. The data may be sourced from various operational systems. Data stored in the information corpus 326 may be structured in a way to specifically address reporting and analytic requirements. In one embodiment, the information corpus may be a relational database (e.g., conform to an ontology). In some example embodiments, data sources 324 may include one or more document repositories.

In certain embodiments, answer generator 328 may be a computer module that generates answers to posed questions. Examples of answers generated by answer generator 328 may include, but are not limited to, answers in the form of natural language sentences; reports, charts, or other analytic representation; raw data; web pages, and the like.

Consistent with various embodiments, answer generator 328 may include query processor 330, visualization processor 332 and feedback handler 334. When information in a data source 324 matching a parsed question is located, a technical query associated with the pattern can be executed by query processor 330. Based on retrieved data by a technical query executed by query processor 330, visualization processor 332 can render visualization of the retrieved data, where the visualization represents the answer. In certain embodiments, visualization processor 332 may render various analytics to represent the answer including, but not limited to, images, charts, tables, dashboards, maps, and the like. In certain embodiments, visualization processor 332 can present the answer to the user in understandable form.

In certain embodiments, feedback handler 334 can be a computer module that processes feedback from users on answers generated by answer generator 328. In certain embodiments, users may be engaged in dialog with the QA system 312 to evaluate the relevance of received answers. Answer generator 328 may produce a list of answers corresponding to a question submitted by a user. The user may rank each answer according to its relevance to the question. In certain embodiments, the feedback of users on generated answers may be used for future question answering sessions.

The various components of the exemplary question answering system described above may be used to implement various aspects of the present disclosure. For example, the client application 308 could be used to receive an input question having a set of query attributes. The question analyzer 314 could, in certain embodiments, be used to determine a relationship between a first preference score and a first ranking for a treatment option by analyzing a set of preference scores with respect to a rank-order. Further, the question answering system 312 could, in certain embodiments, be used to perform a search of an information corpus 326 for data that may be used to generate a set of rationale data for the first treatment option with respect to the first rank. The answer generator 328 can be used generate the set of rationale data for the first treatment option with respect to the first rank, and configure the set of rationale data for a user based on a user profile. Further, the visualization processor 332 can, in certain embodiments, be used to provide the set of rationale data which is configured for the user in a designated display area.

Figure 4:
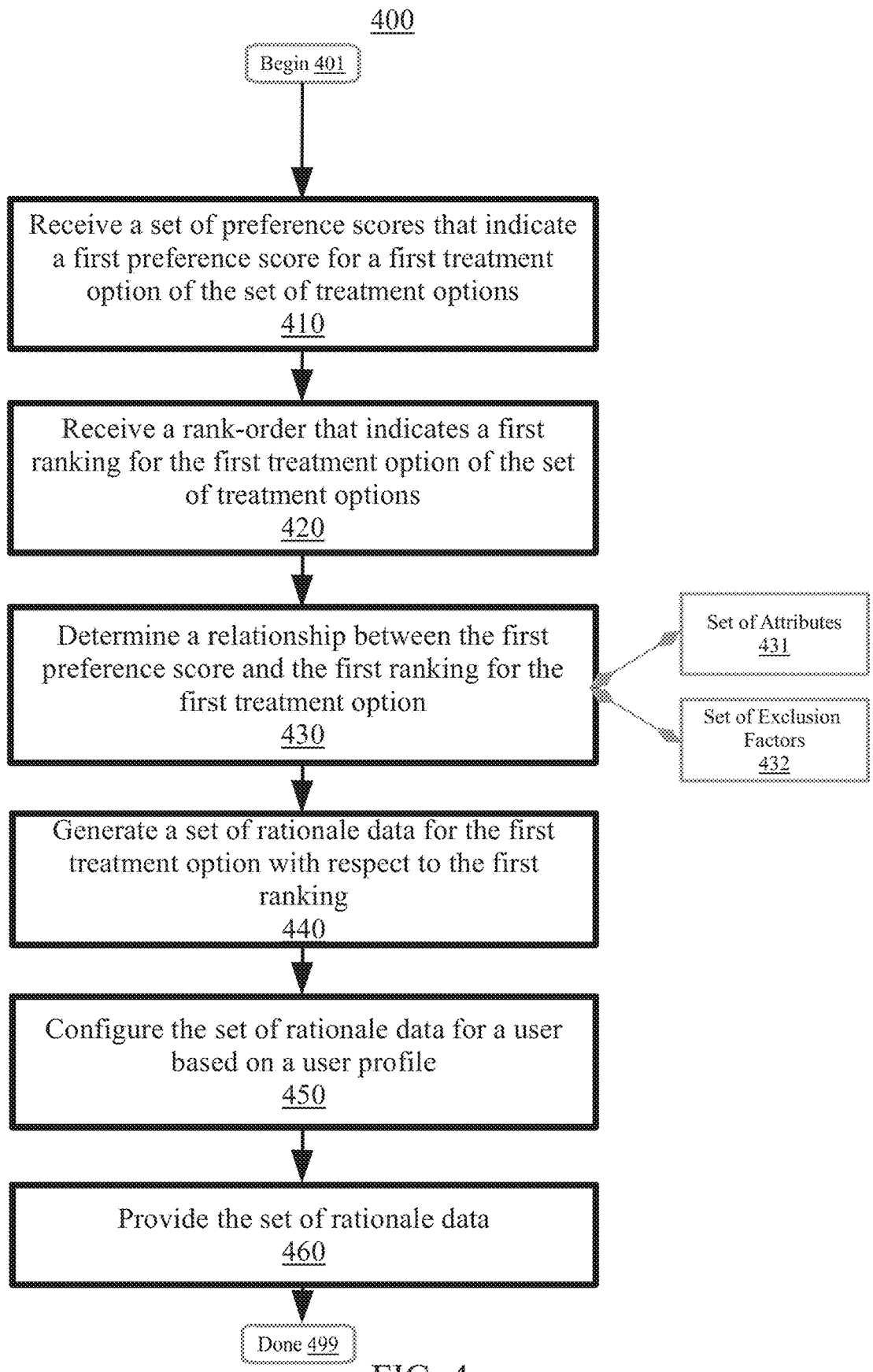
FIG. 4 is a flowchart illustrating a method for generating rationales for a set of treatment options, according to embodiments.

FIG. 4 is a flowchart illustrating a method 400 for generating rationales for a set of treatment options, according to embodiments. Question answering systems are one tool that may be used to provide and rank treatment options for patients. Aspects of the disclosure relate to the recognition that, in some situations, question answering systems may be lacking with respect to provision of evidence-based rationales explaining how and why certain treatment options are ranked as they are. Accordingly, aspects of the disclosure relate to automatic generation of rationale data for a set of treatment options. A rank-order assigned to a set of treatment options may be evaluated with respect to a set of preference scores for the set of treatment options to indicate the degree to which the set of preference scores match the rank-order. Based on a relationship between the set of preference scores and the rank-order, a set of rationale data that indicates the attributes and factors that led to the ranking of a particular treatment option may be dynamically generated. Accordingly, aspects of the method 400 relate to generating a set of rationale data for a first treatment option with respect to a first ranking based on a relationship between a first preference score and a the first ranking for the first treatment option. Generally, the set of treatment options may include a collection of candidate choices regarding care solutions for a user (e.g., patient). For instance, the set of treatment options may include medical care options such as medication prescriptions, therapies, surgeries, prescriptions, regimens (e.g., diet, exercise) operations, or the like. As an example, the set of treatment options may include a list of candidate oncology treatments such as radiation therapy, chemotherapy, stem cell transplants, hormone therapy, immunotherapy, and the like. Other types of treatment options are also possible. The method 400 may begin at block 401.

At block 410, a set of preference scores may be received with respect to the set of treatment options. The set of preference scores may indicate a first preference score for a first treatment option of the set of treatment options. Generally, receiving can include sensing, acquiring, detecting, collecting, obtaining, capturing, ingesting, or otherwise accepting delivery of the set of preference scores with respect to the set of treatment options. The set of preference scores may include a collection of values, grades, weighting factors, ratings, or other parameters that provide a quantitative indication of the appropriateness or suitability of one or more treatment options of the set of treatment options for a user. In embodiments, the set of preference scores may indicate the suitability of a treatment option for a user based on the assumption that the user is not associated with other attributes or factors (e.g., comorbidities) that would affect the treatment (e.g., an ideal patient). In certain embodiments, the set of preference scores may be expressed as integer values between 0 and 10, where lower values indicate lower preference for a treatment option and greater values indicate greater preference for a treatment option (e.g., preference scores of 1-3 may indicate a treatment option is not recommended, preference scores of 4-6 may indicate that a treatment option is for consideration, and preference scores of 7-10 may indicate that a treatment option is recommended). As described herein, the set of preference scores may include a first preference score for a first treatment option. The first preference score may include a particular preference score assigned to a certain treatment option of the set of treatment options. As an example, the first preference score may indicate a value of 2 for a treatment option of dose-dense doxorubicin/cyclophosphamide followed by paclitaxel. In embodiments, receiving the set of preference scores may include collecting the set of preference scores from one or more users (e.g., doctors). In certain embodiments, receiving the set of preference scores may include using a treatment option management engine to compute the set of preference scores for the set of treatment options based on a historical archive of medical records (e.g., clinical trial results, past usages, medical journals, doctors opinions). Other methods of receiving the set of preference scores with respect to the set of treatment options are also possible.

At block 420, a rank-order may be received with respect to the set of treatment options. The rank-order may indicate a first ranking for the first treatment option of the set of treatment options. Generally, receiving can include sensing, acquiring, detecting, collecting, obtaining, capturing, ingesting, or otherwise accepting delivery of the rank-order that indicates the first ranking for the first treatment option of the set of treatment options. The rank-order may include a grouping, arrangement, classification, or organization for the set of treatment options that designates a position for a particular treatment option relative to other treatment options of the set of treatment options. In embodiments, the rank-order may define a hierarchy for the set of treatment options, such that those treatment options located higher within the rank-order are generally associated with greater reliability, suitability, or preference (e.g., with respect to a particular user). As an example, for a set of treatment options of brachytherapy, proton therapy, stereotactic body radiation therapy, and tomotherapy, a rank-order may be received that defines a hierarchy of tomotherapy (e.g., rank 1) followed by proton therapy (e.g., rank 2), brachytherapy (e.g., rank 3), and stereotactic body radiation therapy (e.g., rank 4). As described herein, the rank-order may indicate a first ranking for a first treatment option of the set of treatment options. The first ranking may include a particular ranking (e.g., hierarchical position, rating) for a certain treatment option relative to other treatment options of the set of treatment options. For instance, the rank-order may indicate a first ranking of "2" for a treatment option of intensity-modulated radiation therapy (e.g., the treatment option is ranked second among the list of candidate treatment options). In embodiments, receiving the rank-order may include using a treatment option management engine (e.g., question-answering system) to aggregate a plurality of scores (e.g., the set of preference scores together with a number of other scores), user attributes (e.g., characteristics that describe the condition of a patient), and other factors (e.g., treatment compatibilities, relationship between a treatment option and one or more user attributes) to generate the rank-order for the set of treatment options. Other methods of receiving the rank-order indicating the first ranking for the first treatment option of the set of treatment options with respect to the set of treatment options are also possible.

At block 430, a relationship between the first preference score and the first ranking for the first treatment option may be determined. The relationship may be determined by analyzing the set of preference scores with respect to the rank-order. Generally, determining can include computing, formulating, detecting, extracting, calculating, identifying, or otherwise ascertaining the relationship between the first preference score and the first ranking for the first treatment option. The relationship may include an association, correspondence, interrelation, or correlation between the first preference score and the first ranking for the first treatment option. In embodiments, the relationship may indicate a degree of similarity or disparity between the first preference score and the first ranking for the first treatment option. For instance, the relationship may indicate whether the first preference score substantially matches the first ranking (e.g., the first preference score and the first ranking rate the first treatment option similarly) or whether the first preference score substantially mismatches the first ranking (e.g., the first preference score and the first ranking rate the first treatment option differently). In embodiments, determining the relationship may include analyzing (e.g., examining, appraising, assessing, evaluating) the first preference score with respect to the first ranking to compute a correlation score (e.g., indication of the degree/extent of similarity), and subsequently comparing the correlation score for the first preference score and the first ranking to a designated similarity threshold. As such, preference scores and rankings having correlation scores that achieve the designated similarity threshold may be ascertained to constitute a match, while preference scores and rankings having correlation scores that fail to achieve the designated similarity threshold may be ascertained to constitute a mismatch. Consider the following example. A set of preference scores may include a first preference score for a first treatment option of "9" (e.g., highly recommended), and a rank-order may indicate a first ranking for the first treatment option of "3rd among 50 treatment options." The first preference score and the first ranking may be compared, and a correlation score of "96%" (e.g., the degree of similarity between the first preference score and the first treatment option) may be computed and compared to a designated similarity threshold of "90%." Accordingly, a relationship that indicates a substantial match between the first preference score and the first ranking may be determined. Other methods of determining the relationship between the first preference score and the first ranking for the first treatment option by analyzing the set of preference scores with respect to the rank-order are also possible.

In embodiments, a set of attributes may be detected to determine the relationship between the first preference score and the first ranking for the first treatment option at block 431. The set of attributes may characterize a merit feature of the set of treatment options. Generally, detecting can include sensing, discovering, computing, calculating, distinguishing, ascertaining, or otherwise determining the set of attributes to determine the relationship between the first preference score and the first ranking for the first treatment option. The set of attributes may include a collection of traits, properties, qualities, characteristics, or features of the set of treatment options that contribute to determination of the rank-order for the set of treatment options. In embodiments, the set of attributes may characterize a merit feature of the set of treatment options. The merit feature may include a benefit, advantage, or positive impact associated with the set of treatment options (e.g., that positively impacted the ranking of a treatment option in the rank-order). For instance, the set of attributes may include reasons that the set of treatment options were chosen for a particular user, the types of conditions on which the set of treatment options are effective, or the qualities of the set of treatment options that make them suitable for use. As examples, the set of attributes may include a list of properties such as "effective on tumors less than 4 cm in diameter," "positive impact on stages of N2 or less" or the like. In embodiments, detecting the set of attributes may include parsing a treatment option management database to identify and extract the set of attributes used to determine the rank-order for the set of treatment options. Other methods of detecting the set of attributes to determine the relationship between the first preference score and the first ranking for the first treatment option are also possible.

In embodiments, a set of exclusion factors may be detected to determine the relationship between the first preference score and the first ranking for the first treatment option at block 432. The set of exclusion factors may characterize a demerit feature of the set of treatment options. Generally, detecting can include sensing, discovering, computing, calculating, distinguishing, ascertaining, or otherwise determining the set of exclusion factors to determine the relationship between the first preference score and the first ranking for the first treatment option. The set of exclusion factors may include a collection of traits, properties, qualities, characteristics, or features of the set of set of treatment options that contribute to determination of the rank-order for the set of treatment options. In embodiments, the set of exclusion factors that characterize a demerit feature of the set of treatment options may include a detriment, drawback, disadvantage, or negative impact associated with the set of treatment options (e.g., that negatively impacted the ranking of one or more treatment options in the rank-order). For instance, the set of exclusion factors may include reasons that particular treatment options of the set of treatment options were not chosen for a particular user, why a particular treatment option was not rated more highly in the rank-order, context information that impacted the rank-order, or the like. As examples, the set of exclusion factors may include user age, past medical history, medical conditions, psychological state, user preference, or the like (e.g., user age diminishes the advisability of a treatment option of "surgery" for a particular user). In embodiments, detecting the set of exclusion factors may include parsing a treatment option management database to identify and extract the set of exclusion factors used to determine the rank-order for the set of treatment options. Other methods of detecting the set of exclusion factors to determine the relationship between the first preference score and the first ranking for the first treatment option are also possible.

At block 440, a set of rationale data may be generated. The set of rationale data may be generated for the first treatment option with respect to the first ranking based on the relationship between the first preference score and the first ranking. Generally, generating can include formulating, creating, instantiating, producing, assembling, structuring, arranging, organizing, or otherwise establishing the set of rationale data for the first treatment option with respect to the first ranking based on the relationship between the first preference score and the first ranking. The set of rationale data may include a collection of information that indicates an explanation, reason, motivation, or justification for why one or more treatment options of the set of treatment options are ranked as they are in the rank-order. In embodiments, the set of rationale data may include a portion of the set of attributes, the set of exclusion factors, or both. In embodiments, generating the set of rationale data may include aggregating one or more of a subset of the set of attributes or a subset of the set of exclusion factors based on the relationship between the first preference score and the first ranking. As an example, consider a first treatment option of pneumonectomy for a lung cancer patient. The first treatment option of pneumonectomy may be associated with a first preference score of 8 (e.g., recommended), and be assigned a first ranking of "28th of 30 treatment options" in the rank-order. Accordingly, based on the relationship between the first preference score and the first ranking, a subset of the set of attributes and a subset of the set of exclusion factors for the first treatment option may be aggregated to generate a set of rationale data of "Pneumonectomy is often a recommended treatment for this patient due to attributes of: Efficient removal of affected tissue and prevention of malignant cell spreading; however, due to an exclusion factor for the patient of severe chronic airways disease, other treatments are recommended." As such, the set of rationale data may utilize the set of attributes and the set of exclusion factors to provide a justification/reasoning for why the first treatment option was ranked as it was (e.g., and explain the discrepancy between the first preference score and the first rank). Other methods of generating the set of rationale data for the first treatment option with respect to the first ranking based on the relationship between the first preference score and the first ranking are also possible.

At block 450, the set of rationale data may be configured for a user. The set of rationale data may be configured for the user based on a user profile for the user. Generally, configuring can include formulating, arranging, modifying, organizing, adapting, personalizing, or customizing the set of rationale data for the user based on a user profile for the user. The user profile may include a collection of information or data associated with a specific user (e.g., individual, patient). The user profile may include information regarding the medical history, medical conditions (e.g., comorbidities), prescriptions, age, personality, preferences, and other data for the user. In embodiments, configuring the set of rationale data may include customizing the rationale text based on the user profile. In certain embodiments, configuring may include removing one or more attributes or exclusion factors from the set of rationale data that are not relevant to the user (e.g., an attribute describing the efficacy of a treatment option on tumor treatment may not be relevant to a user who does not have a tumor). In certain embodiments, configuring may include parsing the user profile data for the user to identify one or more elements that are relevant to the set of treatment options, and appending additional sets of rationale data with respect to the identified elements. As an example, for a user with a history of knee pain (e.g., as indicated by the user profile for the user), a set of rationale data for a first treatment option indicating an exercise regimen may be modified to append an additional set of rationale data that describes how the exercise regimen was structured to include activities associated with low-impact to the knees of the user. As such, the set of rationale data may be customized for the user based on the user profile. Other methods of configuring the set of rationale data for the user based on a user profile for the user are also possible.

At block 460, the set of rationale data which is configured for the user may be provided. Generally, providing can include conveying, sending, relaying, supplying, transmitting, delivering, or otherwise presenting the set of rationale data which is configured for the user. In embodiments, providing can include presenting the set of rationale data together with the rank-order for the set of treatment options such that each treatment option of the set of treatment options is associated with an explanation for the attributes and exclusion factors that resulted in its ranking. In certain embodiments, providing may include displaying the set of rationale data in a graphical user interface to be viewed by a user. Consider the following example. A set of treatment options of brachytherapy, proton therapy, stereotactic body radiation therapy and tomotherapy may be associated with a rank-order that defines a hierarchy of tomotherapy (e.g., rank 1) followed by proton therapy (e.g., rank 2), brachytherapy (e.g., rank 3), and stereotactic body radiation therapy (e.g., rank 4). As described herein, a set of rationale data may be generated for the set of treatment options that provides a set of attributes and a set of exclusion factors justifying the rank of each treatment option may be generated for the set of treatment options. Accordingly, providing may include structuring a visual interface layout that allows a user to view each treatment option and associated ranking, together with corresponding rationale data that explains the reasoning for the hierarchy of the set of treatment options. Other methods of providing the set of rationale data which is configured for the user are also possible.

Method 400 concludes at block 499. As described herein, aspects of method 400 relate to generating rationales for a set of treatment options. Aspects of method 400 may provide performance or efficiency benefits related to rationale generation management. As an example, providing a set of rationale data for a set of treatment options may promote treatment option reliability and facilitate treatment option selection (e.g., users may be informed of why particular treatment options are ranked as they are). Leveraging rationale data with respect to a set of treatment options may be associated with benefits such as treatment option ranking validity, accuracy, and rationale generation efficiency. Aspects may save resources such as bandwidth, processing, or memory.

Figure 5:
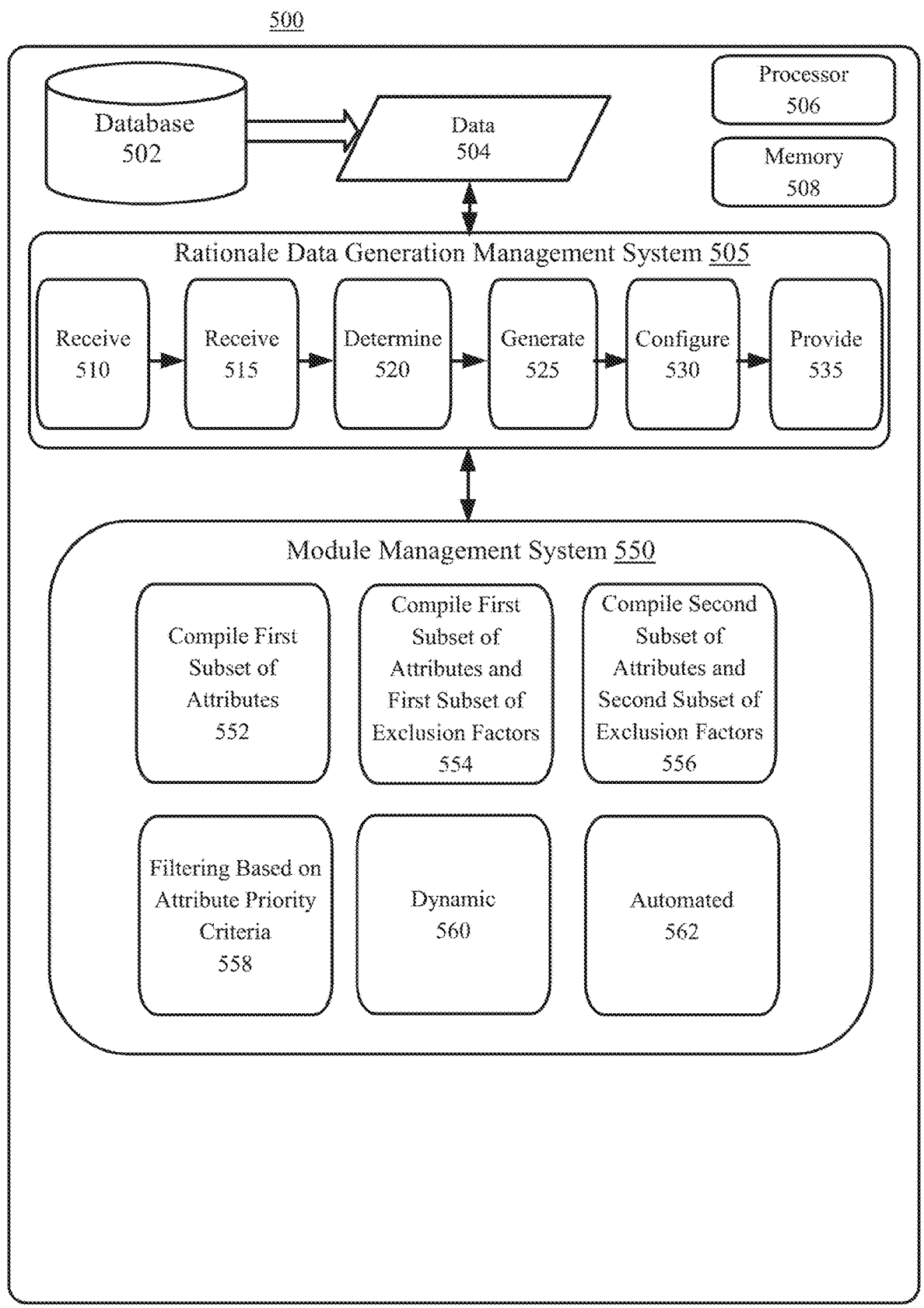
FIG. 5 is a flowchart illustrating a system for generating rationales for a set of treatment options, according to embodiments.

FIG. 5 shows an example system 500 for generating rationales for treatment options, according to embodiments. The example system 500 may include a processor 506 and a memory 508 to facilitate implementation of generating rationales for treatment options. The example system 500 may include a database 502 (e.g., rationale data database). In embodiments, the example system 500 may include a rationale data generation management system 505. The rationale data generation management system 505 may be communicatively connected to the database 502, and be configured to receive data 504 related to rationale data generation (e.g., treatment options, rank orders, preference scores, user profiles). The rationale data generation management system 505 may include a receiving module 510 to receive a set of performance scores, a receiving module 515 to receive a rank-order, a determining module 520 to determine a relationship between a first preference score and a first ranking for a first treatment option, a generating module 525 to generate a set of rationale data, a configuring module 530 to configure the set of rationale data for a user, and a providing module 535 to provide the rationale data. The rationale data generation management system 505 may be communicatively connected with a module management system 550 that includes one or more modules for implementing aspects of generating rationales for a set of treatment options.

In embodiments, it may be determined that the first preference score achieves a match with respect to the first ranking at module 552. The match may be determined based on the relationship between the first preference score and the first ranking. Generally, determining can include computing, formulating, detecting, extracting, calculating, identifying, or otherwise ascertaining the match between the first preference score and the first ranking. The match may include a similarity, congruence, correlation, or correspondence between the first preference score and the first ranking. As an example, the match may indicate that both the first preference score and the first ranking categorize the first treatment option as belonging to the same recommendation category (e.g., recommended, for consideration, not recommended). In embodiments, determining the match may include analyzing the first preference score with respect to the first ranking to compute a correlation score (e.g., indication of the degree/extent of similarity), and subsequently ascertaining that the correlation score for the first preference score and the first ranking achieve a designated similarity threshold. As an example, a first treatment option may be associated with a first preference score of 3 and a ranking of 19th out of 20 treatment options. Accordingly, a correlation score of "98%" (e.g., the degree of similarity between the first preference score and the first treatment option) may be computed and compared to a designated similarity threshold of "90%." Accordingly, as the correlation score of 98% achieves the designated similarity threshold of 90%, it may be determined that the first preference score achieves a match with respect to the first ranking. Other methods of determining that the first preference score achieves a match with respect to the first ranking are also possible.

In embodiments, a first subset of attributes of the set of attributes of the set of attributes may be compiled to generate the set of rationale data in an automated fashion. The first subset of attributes of the set of attributes may correspond to the first treatment option of the set of treatment options. Generally, compiling can include collecting, assembling, accumulating, gathering, or otherwise aggregating the first subset of attributes of the set of attributes to generate the set of rationale data. The first subset of attributes may include a portion of the set of attributes that correspond to (e.g., relate to, are relevant to, associated with) the first treatment option of the set of treatment options. In embodiments, compiling may include summarizing the subset of attributes that led to generation of the first preference score for the first treatment option (e.g., no exclusion factors significantly affected the score, and therefore do not need to be included in the rationale). As an example, consider a first treatment option of "dose dense AC (doxorubicin/cyclophamide)" that is associated with a first preference score of 10 and a first ranking of 1. In response to determining a match between the first preference score and the first ranking, a set of rationale text may be compiled that indicates "dose dense AC (doxorubicin/cyclophosphamide) is a recommended treatment for patients who are HER2 negative, have positive nodes, and a large tumor." Other methods of compiling the first subset of attributes of the set of attributes to generate the set of rationale data in an automated fashion are also possible.

In embodiments, it may be determined that the first preference score fails to achieve a match with respect to the first ranking at module 554. The failure to achieve the match may be determined based on the relationship between the first preference score and the first ranking. Generally, determining can include computing, formulating, detecting, extracting, calculating, identifying, or otherwise ascertaining that the first preference score fails to achieve the match with respect to the first ranking. In embodiments, failing to achieve the match may include detecting a mismatch, dissimilarity, incongruence, divergence, or disparity between the first preference score and the first ranking. As an example, the mismatch may indicate that the first preference score and the first ranking categorize the first treatment option into different recommendation categories (e.g., the first preference score recommends the first treatment option, while the first ranking does not recommend the first treatment option). In embodiments, determining the mismatch may include analyzing the first preference score with respect to the first ranking to compute a correlation score, and subsequently ascertaining that the correlation score for the first preference score and the first ranking does not achieve a designated similarity threshold. As an example, a first treatment option may be associated with a first preference score of 7 (e.g., indicating that the first treatment option is recommended) and a first ranking of 10th out of 10 treatment options (e.g., indicating that the first treatment option is not recommended). Accordingly, a correlation score of 44% may be computed and compared to a designated similarity threshold of 90%, and it may be determined that he first preference score fails to achieve a match with respect to the first ranking. Other methods of determining that the first preference score fails to achieve the match with respect to the first ranking are also possible.

In embodiments, both a first subset of attributes of the set of attributes and a first subset of exclusion factors of the set of exclusion factors may be compiled to generate the set of rationale data in an automated fashion. The first subset of attributes of the set of attributes and the first subset of exclusion factors of the set of exclusion factors may correspond to the first treatment option of the set of treatment options. Generally, compiling can include collecting, assembling, accumulating, gathering, or otherwise aggregating the first subset of attributes of the set of attributes and the first subset of exclusion factors of the set of exclusion factors to generate the set of rationale data. As described herein, the first subset of attributes and the first subset of exclusion factors may include portions of the set of attributes and the set of exclusion factors, respectively, that correspond to (e.g., relate to, are relevant to, associated with) the first treatment option of the set of treatment options. In embodiments, in the event that that the first preference score mismatches the first ranking (e.g., a treatment option has a high or medium preference score, but the first ranking places it in a lower category), compiling may include summarizing the subset of attributes as well as the subset of exclusion factors that resulted in the first ranking for the first treatment option (e.g., attributes and exclusion factors that impacted/contributed to the ranking). As an example, consider that a first treatment option of "dose dense AC (doxorubicin/cyclophosphamide)" is associated with a first preference score of 10 and a first ranking of 7th out of 10 treatment options (e.g., e.g., the first preference score and the first ranking mismatch one another). Accordingly, in response to determining the mismatch between the first preference score and the first ranking, a set of rationale data may be compiled that indicates "dose dense AC (doxorubicin/cyclophosphamide) is often a recommended treatment for patients who are HER2 negative, have positive nodes, and a large tumor; however, due to the patient's grade 3 peripheral neuropathy, this treatment should only be used with caution. There are more preferred treatments available." Other methods of compiling the first subset of attributes of the set of attributes and the first subset of exclusion factors of the set of exclusion factors to generate the set of rationale data in an automated fashion are also possible.

In embodiments, it may be determined that the first preference score achieves a discrepancy threshold with respect to the first ranking at module 556. Achieving of the discrepancy threshold may be determined based on the relationship between the first preference score and the first ranking. Generally, determining can include computing, formulating, detecting, extracting, calculating, identifying, or otherwise ascertaining that the first preference score fails achieves the discrepancy threshold with respect to the first ranking. The discrepancy threshold may include a benchmark, criterion, or reference value that defines a boundary with respect to the correlation between the first preference score and the first ranking. For instance, the discrepancy threshold may include a designated degree of similarity (e.g., dissimilarity) between the first preference score and the first ranking, such that those preference scores that achieve the discrepancy threshold are ascertained to be substantially different, divergent, or incongruous with respect to the first ranking. For instance, the discrepancy threshold may include a designated correlation score of "50%" (e.g., preference scores and rankings having correlation scores of less than 50% may be considered to achieve the discrepancy threshold). As an example, consider that a first treatment option has a first preference score of 2 (e.g., indicating that it is not recommended), but is associated with a first ranking of 3rd of 25 treatment options (e.g., because other treatment options have been ruled out due to various factors). Accordingly, determining may include computing a correlation score of 32% for the first preference score and the first ranking, and subsequently comparing it to the designated correlation score of "50%" defined by the discrepancy threshold. Accordingly, it may be ascertained that the first preference score achieves the discrepancy threshold with respect to the first ranking. Other methods of determining that the first preference score achieves the discrepancy threshold with respect to the first ranking are also possible.

In embodiments, both a second subset of attributes of the set of attributes and a second subset of exclusion factors of the set of exclusion factors that may be compiled to generate the set of rationale data in an automated fashion. The second subset of attributes of the set of attributes and the second subset of exclusion factors of the set of exclusion factors may correspond to a second treatment option of the set of treatment options. Generally, compiling can include collecting, assembling, accumulating, gathering, or otherwise aggregating the second subset of attributes of the set of attributes and the second subset of exclusion factors of the set of exclusion factors to generate the set of rationale data. Aspects of the disclosure relate to the recognition that, in some situations, a treatment option may be associated with a low preference score, but still be ranked highly in the rank-order as a result of other treatment options of the set of treatment options being discarded due to one or more exclusion factors. Accordingly, aspects of the disclosure relate to compiling a set of rationale data to indicate that one or more other treatment options of the set of treatment options have been removed from consideration, and that the ranking for the first treatment option of the set of treatment options has been elevated in the rank-order. In embodiments, compiling the set of rationale data may include analyzing the attributes and exclusion factors associated with the second treatment option to ascertain a second subset of attributes and a second subset of exclusion factors that impacted the ranking of the second treatment with respect to the rank-order for the set of treatment options. As an example, consider that a first treatment option of "carboplatin" that is associated with a first preferred score of 3 (e.g., indicating that it is not recommended), but a rank-order of 2nd out of 10 treatment options (e.g., indicating that it is a recommended treatment). Accordingly, a second set of attributes and a second subset of exclusion factors may be compiled to generate a set of rationale data indicating that "Carboplatin is typically not a recommended treatment for patients who are HER2 negative, have positive nodes, and a large tumor, however the patient's poor creatine clearance has contraindicated the use of paclitaxel-containing regiments and the patient's neuropathy has contraindicated the use of oxaliplatin, therefore carboplatin is recommended out of the options available to the patient." Other methods of compiling both the second subset of attributes of the set of attributes and the second subset of exclusion factors of the set of exclusion factors to generate the set of rationale data in an automated fashion are also possible.

In embodiments, the set of attributes may be filtered at module 558. The set of attributes may be filtered in an automated fashion based on a set of attribute priority criteria to remove a second subset of attributes from the set of attributes. Aspects of the disclosure relate to the recognition that, in some situations, the number of attributes associated with a particular treatment option may exceed a threshold (e.g., 10 or more attributes), and it may not be desirable to include all of them in the set of rationale data. Accordingly, aspects of the disclosure relate to filtering the set of attributes based on a set of attribute priority criteria to remove a second subset of attributes from the set of attributes. Generally, filtering can include removing, separating, refining, arranging, discarding, or otherwise organizing the set of attributes based on the set of attribute priority criteria. The set of attribute priority criteria may include a collection of rules, benchmarks, guidelines, requirements, stipulations, and other parameters that define which attributes are considered to be relevant/germane to a particular treatment option. In embodiments, filtering may include assigning a priority score to one or more attributes based on the set of attribute priority criteria. The priority score may be a quantitative indication of the degree of priority of a particular attribute. As examples, filtering may include prioritizing those attributes that are used with respect to both preference score determination and exclusion factor determination, attributes that are associated with "Required" tags (e.g., as opposed to "Optional"), attributes that impact the preference score for one or more treatment options (e.g., if changing the value of an attribute of "HER2Status" from positive to negative would impact the preference score of a treatment option, the attribute may be prioritized according to the level of impact it would have on the preference score), or attributes included in training cases or historical cohorts for patients. Accordingly, priority scores may be assigned to each attribute of the set of attributes, and the set of attributes may subsequently be filtered to remove those attributes that do not achieve a threshold priority score from the set of rationale data (e.g., remove those attributes with priority scores of less than 75). Other methods of filtering the set of attributes in an automated fashion based on a set of attribute priority criteria are also possible.

In embodiments, the receiving, the receiving, the determining, the generating, the configuring, the providing, and the other steps described herein may each be executed in a dynamic fashion at module 560. The steps described herein may be executed in a dynamic fashion to streamline rationale data generation for a set of treatment options. For instance, the receiving, the receiving, the determining, the generating, the configuring, the providing, and the other steps described herein may occur in real-time, ongoing, or on-the-fly. As an example, one or more steps described herein may be performed on-the-fly (e.g., sets of rationale data may be dynamically generated, configured based on user profiles, and provided for users as sets of preference scores and rank-orders for a set of treatment options are received in real-time) in order to streamline (e.g., facilitate, promote, enhance) rationale data generation for a set of treatment options. Other methods of performing the steps described herein are also possible.

In embodiments, the receiving, the receiving, the determining, the generating, the configuring, the providing, and the other steps described herein may each be executed in an automated fashion at block 562. The steps described herein may be executed in an automated fashion without user intervention. In embodiments, the receiving, the receiving, the determining, the generating, the configuring, the providing, and the other steps described herein may be carried out by an internal rationale data generation management module maintained in a persistent storage device of a local computing device (e.g., network node). In embodiments, the receiving, the receiving, the determining, the generating, the configuring, the providing, and the other steps described herein may be carried out by an external rationale data generation management module hosted by a remote computing device or server (e.g., server accessible via a subscription, usage-based, or other service model). In this way, aspects of rationale data generation for a set of treatment options may be performed using automated computing machinery without manual action. Other methods of performing the steps described herein are also possible.

Figure 6:
FIG. 6 depicts an example of generating rationales for a set of treatment options, according to embodiments.

FIG. 6 depicts an example of generating rationales for a set of treatment options, according to embodiments. In embodiments, a graphical user interface 600 may be used to provide a visual representation of a set of treatment options. As described herein, the set of treatment options may be associated with a set of preference scores that provide a quantitative indication of the appropriateness or suitability of one or more treatment options of the set of treatment options for a user. In embodiments, the set of preference scores may indicate the suitability of a treatment option for a user based on the assumption that the user is not associated with other attributes or factors (e.g., comorbidities) that would affect the treatment (e.g., an ideal patient). In embodiments, the set of treatment options may be associated with a rank-order that defines a hierarchy for the set of treatment options, such that those treatment options located higher within the rank-order are generally associated with greater reliability, suitability, or preference (e.g., with respect to a particular user). Other methods of using a graphical user interface 600 to illustrate a set of treatment options are also possible.

FIG. 7 depicts an example of generating rationales for a set of treatment options, according to embodiments. In embodiments, a preference score index 700 may be utilized to determine a recommendation for a treatment option of the set of treatment options based on a set of preference scores for the set of treatment options (e.g., in the event that other attributes or exclusion factors do not impact the ranking of the set of treatment options). For instance, as shown in the preference score index 700, treatment options associated with a preference score between 1 and 3 may be categorized as "not recommended," treatment options associated with a preference score between 4 and 6 may be categorized as "for consideration," and treatment options associated with a preference score between 7 and 10 may be categorized as recommended. Other methods of using the set of preference scores to categorize the set of treatment options are also possible.

FIG. 8 depicts an example of generating rationales for a set of treatment options, according to embodiments. In embodiments, a rationale data generation rubric 800 may be used to facilitate generation of the set of rationale data for a set of treatment options. As described herein, in the event that the preference score for a treatment option achieves a match with respect to the ranking (e.g., preference score is high and treatment is green/recommended, preference score is medium and treatment is yellow/for consideration, preference score is low and treatment is red/not recommended) for the treatment specified by the rank-order, the set of rationale data may be generated by summarizing the attributes that contribute to computation of the preference score (e.g., no other factors significantly affected the score and therefore don't need to be included). In the event that a treatment option is associated with a preference score that does not match the ranking specified by the rank-order (e.g., treatment option has a high or medium preference score, but the rank-order places it in a lower category such as red/not recommended), the set of rationale data may be generated by summarizing the attributes as well as the exclusion factors that have influenced the ranking of the treatment option. In certain embodiments, in the event that a first treatment option is associated with a low preference score but is ranked substantially highly in the rank-order (e.g., other treatment options have been discarded/ruled-out based on exclusion factors), the set of rationale data may be generated by summarizing the attributes and exclusion factors that resulted in discarding of the other treatment options that were in consideration with respect to the first treatment operation. Other methods of generating the set of rationale data are also possible.

In addition to embodiments described above, other embodiments having fewer operational steps, more operational steps, or different operational steps are contemplated. Also, some embodiments may perform some or all of the above operational steps in a different order. In embodiments, operational steps may be performed in response to other operational steps. The modules are listed and described illustratively according to an embodiment and are not meant to indicate necessity of a particular module or exclusivity of other potential modules (or functions/purposes as applied to a specific module).

In the foregoing, reference is made to various embodiments. It should be understood, however, that this disclosure is not limited to the specifically described embodiments. Instead, any combination of the described features and elements, whether related to different embodiments or not, is contemplated to implement and practice this disclosure. Many modifications and variations may be apparent to those of ordinary skill in the art without departing from the scope and spirit of the described embodiments. Furthermore, although embodiments of this disclosure may achieve advantages over other possible solutions or over the prior art, whether or not a particular advantage is achieved by a given embodiment is not limiting of this disclosure. Thus, the described aspects, features, embodiments, and advantages are merely illustrative and are not considered elements or limitations of the appended claims except where explicitly recited in a claim(s).

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

Embodiments according to this disclosure may be provided to end-users through a cloud-computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud-computing resources are provided to a user on a pay-per-use basis, where users are charged only for the computing resources actually used (e.g., an amount of storage space used by a user or a number of virtualized systems instantiated by the user). A user can access any of the resources that reside in the cloud at any time, and from anywhere across the Internet. In context of the present disclosure, a user may access applications or related data available in the cloud. For example, the nodes used to create a stream computing application may be virtual machines hosted by a cloud service provider. Doing so allows a user to access this information from any computing system attached to a network connected to the cloud (e.g., the Internet).

Embodiments of the present disclosure may also be delivered as part of a service engagement with a client corporation, nonprofit organization, government entity, internal organizational structure, or the like. These embodiments may include configuring a computer system to perform, and deploying software, hardware, and web services that implement, some or all of the methods described herein. These embodiments may also include analyzing the client's operations, creating recommendations responsive to the analysis, building systems that implement portions of the recommendations, integrating the systems into existing processes and infrastructure, metering use of the systems, allocating expenses to users of the systems, and billing for use of the systems.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the foregoing is directed to exemplary embodiments, other and further embodiments of the invention may be devised without departing from the basic scope thereof, and the scope thereof is determined by the claims that follow. The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to explain the principles of the embodiments, the practical application or technical improvement over technologies found in the marketplace, or to enable others of ordinary skill in the art to understand the embodiments disclosed herein.

The terminology used herein is for the purpose of describing particular embodiments only and is not intended to be limiting of the various embodiments. As used herein, the singular forms "a," "an," and "the" are intended to include the plural forms as well, unless the context clearly indicates otherwise. "Set of," "group of," "bunch of," etc. are intended to include one or more. It will be further understood that the terms "includes" and/or "including," when used in this specification, specify the presence of the stated features, integers, steps, operations, elements, and/or components, but do not preclude the presence or addition of one or more other features, integers, steps, operations, elements, components, and/or groups thereof. In the previous detailed description of exemplary embodiments of the various embodiments, reference was made to the accompanying drawings (where like numbers represent like elements), which form a part hereof, and in which is shown by way of illustration specific exemplary embodiments in which the various embodiments may be practiced. These embodiments were described in sufficient detail to enable those skilled in the art to practice the embodiments, but other embodiments may be used and logical, mechanical, electrical, and other changes may be made without departing from the scope of the various embodiments. In the previous description, numerous specific details were set forth to provide a thorough understanding the various embodiments. But, the various embodiments may be practiced without these specific details. In other instances, well-known circuits, structures, and techniques have not been shown in detail in order not to obscure embodiments.

What is claimed is:

1. A computer-implemented method for automatically generating rationales for a set of treatment options, the method comprising:

receiving, with respect to the set of treatment options, a set of preference scores that indicates a first preference score for a first treatment option of the set of treatment options, wherein receiving the set of preference scores includes using a treatment option management engine to compute the set of preference scores for the set of treatment options based on a historical archive of medical records;

receiving, with respect to the set of treatment options, a rank-order that indicates a score hierarchy of treatment options containing a first ranking for the first treatment option of the set of treatment options;

computing a correlation score based on analyzing the first preference score and the first ranking, wherein the set of preference scores are expressed as integer values between 0 and 10;

aggregating one or more subsets of a set of attributes and one or more subsets of a set of exclusion factors to generate a set of rationale data for the first treatment option with respect to the first ranking, based on the relationship between the first preference score and the first ranking;

configuring, based on a user profile for a user, the set of rationale data for the user; and providing the set of rationale data which is configured for the user.

2. The method of claim 1, further comprising:

detecting a set of attributes to determine the relationship between the first preference score and the first ranking for the first treatment option, wherein the set of attributes define a merit feature of the set of treatment options, and wherein the merit feature comprises any one or more of a collection of traits, properties, qualities, characteristics, or features of the set of treatment options that contribute to a determination of the rank-order for the set of treatment options.

3. The method of claim 2, further comprising:

detecting a set of exclusion factors to determine the relationship between the first preference score and the first ranking for the first treatment option, wherein the set of exclusion factors define a demerit feature of the set of treatment options, and wherein the demerit feature comprises any one or more of a collection of traits, properties, qualities, characteristics, or features of the set of treatment options that contribute to a determination of the rank-order for the set of treatment options.

4. The method of claim 3, further comprising:

determining, based on the relationship between the first preference score and the first ranking, that the first preference score achieves a match with respect to the first ranking; and compiling, to generate the set of rationale data in an automated fashion, a first subset of attributes of the set of attributes that corresponds to the first treatment option of the set of treatment options.

5. The method of claim 3, further comprising:
determining, based on the relationship between the first preference score and the first ranking, that the first preference score fails to achieve a match with respect to the first ranking; and
compiling, to generate the set of rationale data in an automated fashion, both a first subset of attributes of the set of attributes that corresponds to the first treatment option of the set of treatment options and a first subset of exclusion factors of the set of exclusion factors that corresponds to the first treatment option of the set of treatment options.

6. The method of claim 3, further comprising:
determining, based on the relationship between the first preference score and the first ranking, that the first preference score achieves a discrepancy threshold with respect to the first ranking; and
compiling, to generate the set of rationale data in an automated fashion, both a second subset of attributes of the set of attributes that corresponds to a second treatment option of the set of treatment options and a second subset of exclusion factors of the set of exclusion factors that corresponds to the second treatment option of the set of treatment options.

7. The method of claim 3, further comprising:
filtering, in an automated fashion based on a set of attribute priority criteria, the set of attributes to remove a second subset of attributes from the set of attributes.

8. The method of claim 1, further comprising:
executing, in a dynamic fashion to streamline generating rationales for the set of treatment options, each of:
the receiving, the receiving, the determining, the generating, the configuring, and the providing.

9. The method of claim 1, further comprising:
executing, in an automated fashion without user intervention, each of:
the receiving, the receiving, the determining, the generating, the configuring, and the providing.

10. A system for automatically generating rationales for a set of treatment options, the system comprising:
a memory having a set of computer readable computer instructions, and
a processor for executing the set of computer readable instructions, the set of computer readable instructions including:
receiving, with respect to the set of treatment options, a set of preference scores that indicates a first preference score for a first treatment option of the set of treatment options, wherein receiving the set of preference scores includes using a treatment option management engine to compute the set of preference scores for the set of treatment options based on a historical archive of medical records;
receiving, with respect to the set of treatment options, a rank-order that indicates a score hierarchy of treatment options containing a first ranking for the first treatment option of the set of treatment options;
computing a correlation score based on analyzing the first preference score and the first ranking, wherein the set of preference scores are expressed as integer values between 0 and 10;
aggregating one or more subsets of a set of attributes and one or more subsets of a set of exclusion factors to generate a set of rationale data for the first treatment option with respect to the first ranking, based on the relationship between the first preference score and the first ranking;
configuring, based on a user profile for a user, the set of rationale data for the user; and
providing the set of rationale data which is configured for the user.

11. The method of claim 10, further comprising:
detecting a set of attributes to determine the relationship between the first preference score and the first ranking for the first treatment option, wherein the set of attributes define a merit feature of the set of treatment options, and wherein the merit feature comprises any one or more of a collection of traits, properties, qualities, characteristics, or features of the set of treatment options that contribute to a determination of the rank-order for the set of treatment options.

12. The method of claim 11, further comprising:
detecting a set of exclusion factors to determine the relationship between the first preference score and the first ranking for the first treatment option, wherein the set of exclusion factors define a demerit feature of the set of treatment options, and wherein the demerit feature comprises any one or more of a collection of traits, properties, qualities, characteristics, or features of the set of treatment options that contribute to a determination of the rank-order for the set of treatment options.

13. The system of claim 12, further comprising:
determining, based on the relationship between the first preference score and the first ranking, that the first preference score achieves a match with respect to the first ranking; and
compiling, to generate the set of rationale data in an automated fashion, a first subset of attributes of the set of attributes that corresponds to the first treatment option of the set of treatment options.

14. The system of claim 12, further comprising:
determining, based on the relationship between the first preference score and the first ranking, that the first preference score fails to achieve a match with respect to the first ranking; and
compiling, to generate the set of rationale data in an automated fashion, both a first subset of attributes of the set of attributes that corresponds to the first treatment option of the set of treatment options and a first subset of exclusion factors of the set of exclusion factors that corresponds to the first treatment option of the set of treatment options.

15. The method of claim 12, further comprising:
determining, based on the relationship between the first preference score and the first ranking, that the first preference score achieves a discrepancy threshold with respect to the first ranking; and
compiling, to generate the set of rationale data in an automated fashion, both a second subset of attributes of the set of attributes that corresponds to a second treatment option of the set of treatment options and a second subset of exclusion factors of the set of exclusion factors that corresponds to the second treatment option of the set of treatment options.

16. The system of claim 12, further comprising:
filtering, in an automated fashion based on a set of attribute priority criteria, the set of attributes to remove a second subset of attributes from the set of attributes.

17. The system of claim 10, further comprising:
executing, in a dynamic fashion to streamline generating rationales for the set of treatment options, each of:
the receiving, the receiving, the determining, the generating, the configuring, and the providing.

18. The system of claim 10, further comprising:
executing, in an automated fashion without user intervention, each of:
the receiving, the receiving, the determining, the generating, the configuring, and the providing.

19. A computer program product for automatically generating rationales for a set of treatment options, the computer program product comprising a computer readable storage medium having program instructions embodied therewith, wherein the computer readable storage medium is not a transitory signal per se, the program instructions executable by a processor to cause the processor to perform a method comprising:
receiving, with respect to the set of treatment options, a set of preference scores that indicates a first preference score for a first treatment option of the set of treatment options, wherein receiving the set of preference scores includes using a treatment option management engine to compute the set of preference scores for the set of treatment options based on a historical archive of medical records;
receiving, with respect to the set of treatment options, a rank-order that indicates a score hierarchy of treatment options containing a first ranking for the first treatment option of the set of treatment options;
computing a correlation score based on analyzing the first preference score and the first ranking, wherein the set of preference scores are expressed as integer values between 0 and 10;
aggregating one or more subsets of a set of attributes and one or more subsets of a set of exclusion factors to generate a set of rationale data for the first treatment option with respect to the first ranking, based on the relationship between the first preference score and the first ranking;
configuring, based on a user profile for a user, the set of rationale data for the user; and
providing the set of rationale data which is configured for the user.

20. The computer program product of claim 19, further comprising:
detecting, to determine the relationship between the first preference score and the first ranking for the first treatment option, a set of attributes that characterize a merit feature of the set of treatment options;
detecting, to determine the relationship between the first preference score and the first ranking for the first treatment option, a set of exclusion factors that characterize a demerit feature of the set of treatment options;
determining, based on the relationship between the first preference score and the first ranking, that the first preference score achieves a match with respect to the first ranking;
compiling, to generate the set of rationale data in an automated fashion, a first subset of attributes of the set of attributes that corresponds to the first treatment option of the set of treatment options;
determining, based on the relationship between the first preference score and the first ranking, that the first preference score fails to achieve a match with respect to the first ranking;
compiling, to generate the set of rationale data in an automated fashion, both a first subset of attributes of the set of attributes that corresponds to the first treatment option of the set of treatment options and a first subset of exclusion factors of the set of exclusion factors that corresponds to the first treatment option of the set of treatment options;
determining, based on the relationship between the first preference score and the first ranking, that the first preference score achieves a discrepancy threshold with respect to the first ranking;
compiling, to generate the set of rationale data in an automated fashion, both a second subset of attributes of the set of attributes that corresponds to a second treatment option of the set of treatment options and a second subset of exclusion factors of the set of exclusion factors that corresponds to the second treatment option of the set of treatment options; and
filtering, in an automated fashion based on a set of attribute priority criteria, the set of attributes to remove a second subset of attributes from the set of attributes.

* * * * *